United States Patent
Wang et al.

(10) Patent No.: US 7,013,034 B2
(45) Date of Patent: Mar. 14, 2006

(54) METHODS AND APPARATUS FOR RECONSTRUCTING AN IMAGE OF AN OBJECT

(75) Inventors: Sharon X. Wang, Schaumburg, IL (US); Thomas L. Toth, Brookfield, WI (US); Piero U. Simoni, New Berlin, WI (US); Stephen W. Metz, Greenfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 686 days.

(21) Appl. No.: 10/268,323

(22) Filed: Oct. 10, 2002

(65) Prior Publication Data

US 2004/0071329 A1    Apr. 15, 2004

(51) Int. Cl.
*G06K 9/00* (2006.01)

(52) U.S. Cl. .......................... 382/131; 382/274; 378/4; 250/370.09

(58) Field of Classification Search ................ 382/128, 382/129, 130, 131, 132, 133, 134, 149, 154, 382/169, 172, 219, 274, 289, 291, 294, 318; 378/4, 15, 163; 600/436, 437; 250/370.09
See application file for complete search history.

(56) References Cited

U.S. PATENT DOCUMENTS

| | | | |
|---|---|---|---|
| 5,541,970 A | | 7/1996 | Hu |
| 5,559,847 A | * | 9/1996 | Hu et al. .................. 378/4 |
| 5,606,585 A | * | 2/1997 | Hu .......................... 378/15 |
| 5,761,333 A | * | 6/1998 | Hsieh et al. ............. 382/131 |
| 5,818,896 A | | 10/1998 | Hsieh |
| 5,960,056 A | | 9/1999 | Lai |
| 5,991,356 A | | 11/1999 | Horiuchi et al. |
| 6,278,767 B1 | * | 8/2001 | Hsieh ....................... 378/163 |
| 6,301,325 B1 | * | 10/2001 | Besson et al. ............. 378/15 |
| 6,317,509 B1 | * | 11/2001 | Simanovsky et al. ...... 382/131 |
| 6,345,113 B1 | * | 2/2002 | Crawford et al. .......... 382/131 |
| 6,408,042 B1 | * | 6/2002 | Hsieh ......................... 378/4 |
| 6,522,714 B1 | * | 2/2003 | Wang et al. ................ 378/15 |

* cited by examiner

*Primary Examiner*—Sanjiv Shah
*Assistant Examiner*—Seyed Azarian
(74) *Attorney, Agent, or Firm*—Carl B. Horton, Esq.; Armstrong Teasdale LLP

(57) ABSTRACT

A method for reconstructing an image of an object utilizing a computed tomographic (CT) imaging system having a radiation source configured to project a beam of radiation through an object and towards a multislice detector array configured to sense attenuation of the radiation passing through the object; the method includes helically scanning an object to acquire a plurality of slices of projection data, generating a separate projection dataset for each of N separate detector rows wherein the separate projection datasets include detector row projection data and detector row conjugate projection data, combining the detector row projection data and the detector row conjugate projection data, and helically weighting the combined projection data using a combined helical weighting and conjugate data weighting algorithm such that a greater weight is applied to combined center row projection data than to at least one outermost detector row projection data.

15 Claims, 3 Drawing Sheets

RWT, P=7, slice thickness=1.31mm

METHODS AND APPARATUS FOR RECONSTRUCTING AN IMAGE OF AN OBJECT

BACKGROUND OF THE INVENTION

This invention relates generally to methods and apparatus for computed tomographic (CT) image reconstruction, and more particularly to methods for view weighting of computed tomographic image data.

At least one known computed tomography (CT) imaging system uses an increased table speed to reduce a required scan time. An increased table speed reduces the quantity of data samples acquired along a plurality of helical trajectories within an image reconstruction space. A reduction in the quantity of data samples combined with a plurality of cone beam effects can produce an image with decreased image quality.

BRIEF DESCRIPTION OF THE INVENTION

In one aspect, a method for reconstructing an image of an object utilizing a computed tomographic (CT) imaging system is provided. The CT imaging system includes a radiation source and a multislice detector array on a rotating gantry. The radiation source is configured to project a beam of radiation through an object and towards the multislice detector array, with the multislice detector array configured to sense attenuation of the radiation passing through the object. The method includes helically scanning an object with a computed tomographic imaging system with a helical pitch p that satisfies $0<p\leq 1.5N$ to acquire a plurality of slices of projection data, where N is an even integer quantity of detector rows and p is an odd integer, generating a separate projection dataset for each of the N separate detector rows wherein the separate projection datasets include detector row projection data and detector row conjugate projection data, combining the detector row projection data and the detector row conjugate projection data, and helically weighting the combined projection data using a combined helical weighting and conjugate data weighting algorithm such that a greater weight is applied to combined center row projection data than to at least one outermost detector row projection data.

In another aspect, a computed tomographic (CT) imaging system for reconstructing an image of an object is provided. The CT imaging system includes a radiation source and a multislice detector array on a rotating gantry. The radiation source is configured to project a beam of radiation through an object and towards the multislice detector array, with the multislice detector array configured to sense attenuation of the radiation passing through the object. The imaging system is configured to helically scan an object with a computed tomographic imaging system with a helical pitch p that satisfies $0<p\leq 1.5N$ to acquire a plurality of slices of projection data, where N is an even integer quantity of detector rows and p is an odd integer, generate a separate projection dataset for each of the N separate detector rows wherein the separate projection datasets include detector row projection data and detector row conjugate projection data combine the detector row projection data and the detector row conjugate projection data, and helically weight the combined projection data using a combined helical weighting and conjugate data weighting algorithm such that a greater weight is applied to combined center row projection data than to at least one outermost detector row projection data.

In still another aspect, a computer for collecting computed tomography (CT) scan data is provided. The computer is programmed to helically scan an object with a computed tomographic imaging system with a helical pitch p that satisfies $0<p\leq 1.5N$ to acquire a plurality of slices of projection data, where N is an even integer quantity of detector rows and p is an odd integer, generate a separate projection dataset for each of the N separate detector rows wherein the separate projection datasets include detector row projection data and detector row conjugate projection data, combine the detector row projection data and the detector row conjugate projection data, and helically weight the combined projection data using a combined helical weighting and conjugate data weighting algorithm such that a greater weight is applied to combined center row projection data than to at least one outermost detector row projection data.

DETAILED DESCRIPTION OF THE INVENTION

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
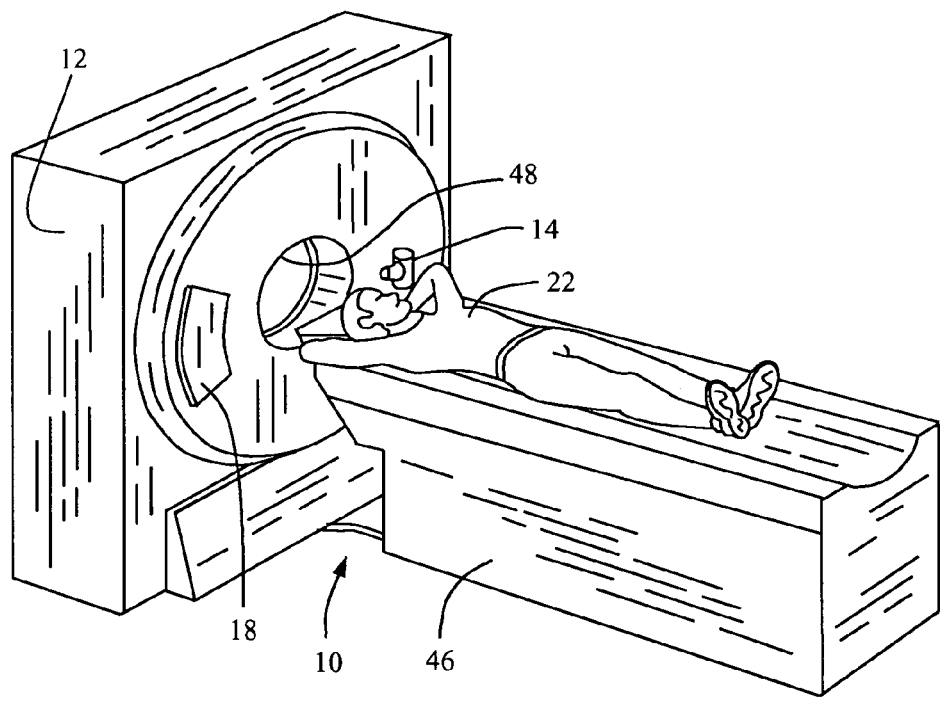
FIG. 1 is a pictorial view of a CT imaging system embodiment.
Figure 2:
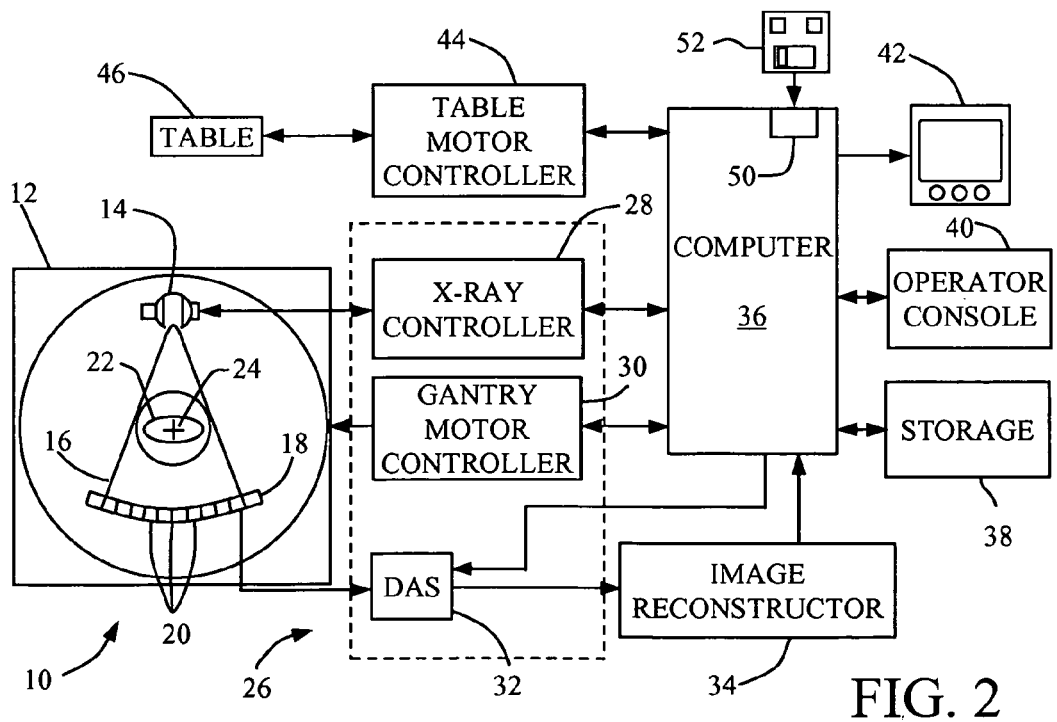
FIG. 2 is a block schematic diagram of the system illustrated in FIG. 1.
Figure 3:
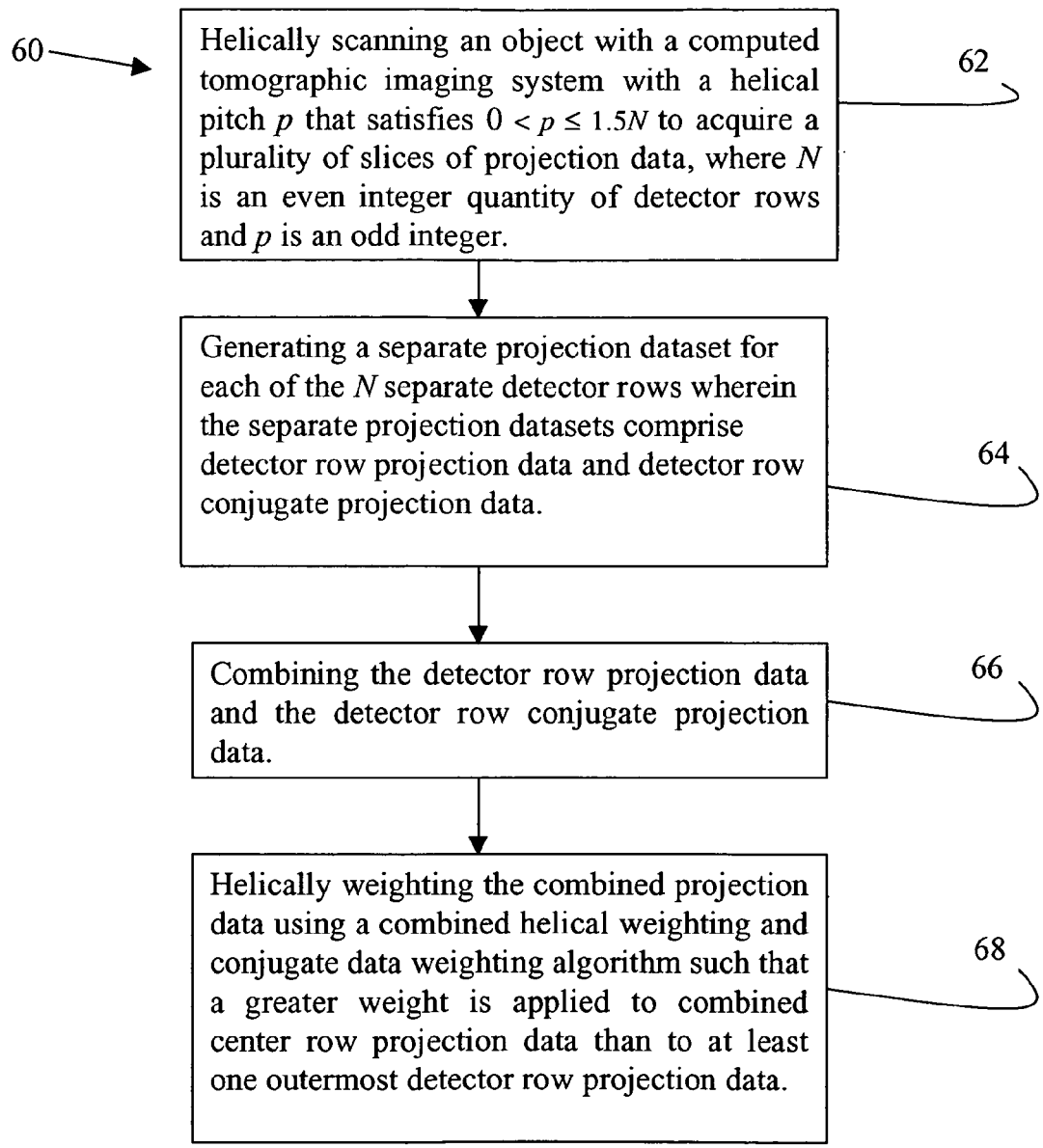
FIG. 3 is a method for reconstructing an image of an object.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes an radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

One embodiment of the present invention utilizes a row-wise thin (RWT) interpolation algorithm for helical scan weighting. RWT view weighting is based on a trajectory of detector 18 during a helical scan and is both simple and highly efficient. In an exemplary embodiment, a method 60 for reconstructing an image of an object includes helically scanning 62 an object with a computed tomographic imaging system with a helical pitch p that satisfies $0<p\leq 1.5N$ to acquire a plurality of slices of projection data, where N is an even integer quantity of detector rows and p is an odd integer, generating 64 a separate projection dataset for each of the N separate detector rows wherein the separate projection datasets comprise detector row projection data and detector row conjugate projection data, combining 66 the detector row projection data and the detector row conjugate projection data, and helically weighting 68 the combined projection data using a combined helical weighting and conjugate data weighting algorithm such that a greater weight is applied to combined center row projection data than to at least one outermost detector row projection data.

Figure 4:
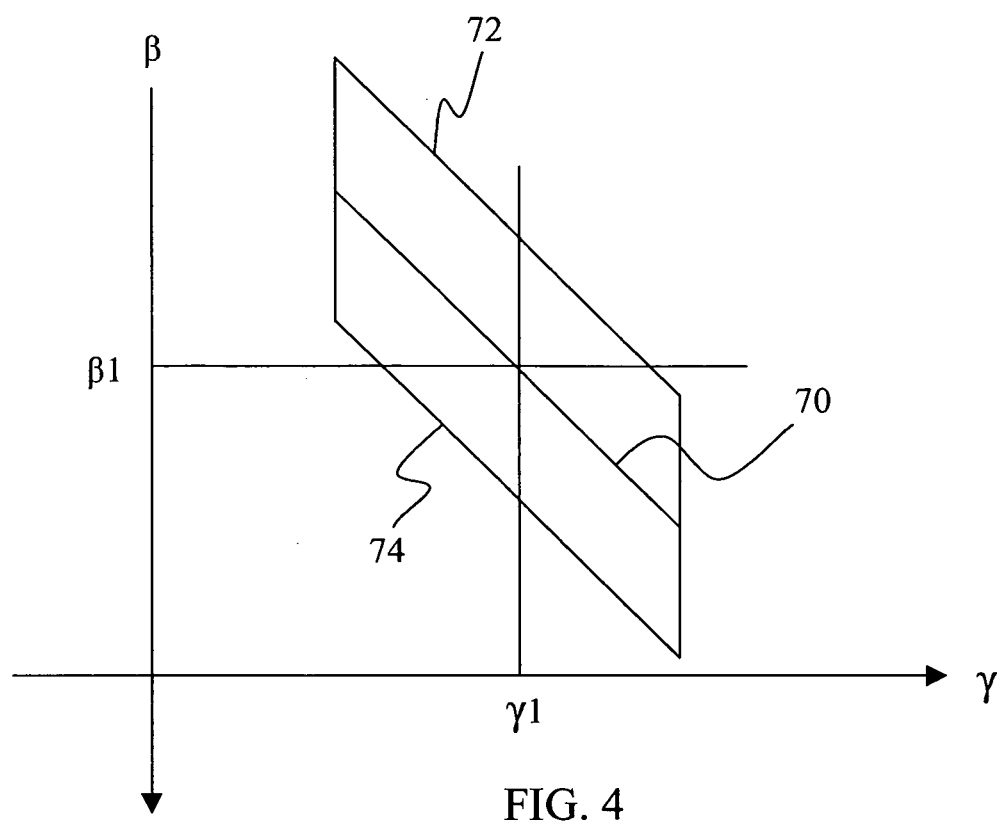
FIG. 4 is graph illustrating an exemplary weighting algorithm in accordance with FIG. 3.

FIG. 4 is graph illustrating a Row-Wise Thin (RWT) helical weighting algorithm. As shown in FIG. 4, a gantry angle β corresponds to a selected slice image within which an image is generated. Lines 72, 70, and 74 correspond to weighting values of two, one, and two, respectively, with the region between lines 72 and 70 varying from zero to one and the region between lines 70 and 74 varying from one to zero. Therefore, the weight values vary as a function of both the gantry angle β and the fan angle γ within specific rows of detector 18 (i.e. within a view corresponding to a specific gantry angle β). For example, for the row view corresponding to gantry angle β1 within the selected plane, a central ray γ1 has a weight value of one while other rays within the row view have weights ranging from zero to one. In the exemplary embodiment, object 22 is helically scanned with an odd integer pitch p that satisfies $0<p\leq 1.5N$ to acquire a plurality of slices of projection data, where N is an even integer quantity of detector rows. As shown, slope of line 70 affects the weighting function and therefore is important. In the exemplary embodiment, using method 60, $t_g$ is set equal to one.

In the exemplary embodiment, a separate projection dataset is generated for each of the N separate detector rows wherein the separate projection datasets include a center detector row projection data and a center detector row conjugate projection data. The center detector row projection dataset and the center detector row conjugate projection dataset are then combined. The combined data is then helically weighted using a combined helical weighting and conjugate data weighting algorithm such that a greater weight is applied to combined center row projection data than to at least one outermost detector row projection data. Outermost detector rows are those detector rows furthest from the isocenter.

In use, for row r, if a point $t(\beta, \gamma)$ in Radon space has a conjugate pair $t'(\beta', \gamma')$, where $\beta'=\beta+\pi+2\gamma$, and $\gamma'=-\gamma$, then the helical weighting function can be written in accordance with:

$$w_r(\beta, \gamma) = \begin{cases} 0, & \beta > \beta_{r3} \\ 1 - \dfrac{\beta - \beta_{r2}}{\Delta\beta}, & \beta_{r3} > \beta > \beta_{r2} \\ 1 + \dfrac{\beta - \beta_{r2}}{\Delta\beta}, & \beta_{r2} > \beta > \beta_{r1} \\ 0, & \beta < \beta_{r1} \end{cases}$$

where:
β is a gantry angle;
γ is a fan angle;
r is a detector row;
p is a helical pitch;

$$\Delta\beta = \frac{\pi}{p};$$

$\beta_{r3} = \gamma + r\Delta\beta$;

$\beta_{r1} = \beta_{r3} + 2\Delta\beta$; and $\beta_{r2} = \beta_{r3} + \Delta\beta$.

In an alternative embodiment, if a point t(β, γ) in Radon space does not have a conjugate pair, then the weighting function can be written in accordance with:

$$w_r(\beta, \gamma) = \begin{cases} 0, & \beta > \beta_{r3} \\ 1 - \dfrac{\beta - \beta_{r2}}{\Delta\beta}, & \beta_{r3} > \beta > \beta_{r2} \\ 1 + \dfrac{\beta - \beta_{r2}}{\Delta\beta}, & \beta_{r2} > \beta > \beta_{r1} \\ 0, & \beta < \beta_{r1} \end{cases}$$

where:
β is a gantry angle;
γ is a fan angle;
r is a detector row;
p is a helical pitch;

$$\Delta\beta = \frac{2\pi}{p};$$

$\beta_{r3} = \gamma + r\Delta\beta$;

$\beta_{r1} = \beta_{r3} + 2\Delta\beta$; and $\beta_{r2} = \beta_{r3} + \Delta\beta$.

Figure 5:
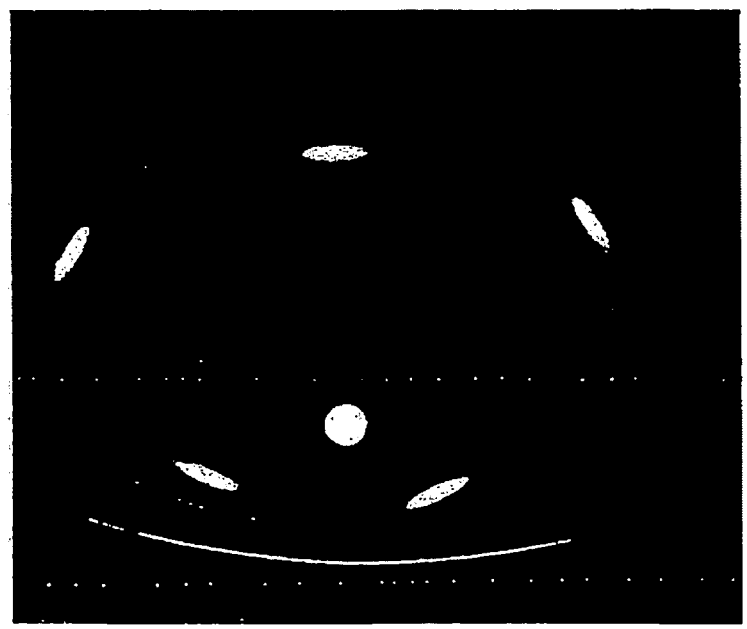
FIG. 5 is a representation of a rebin buffer of one embodiment of the present invention.

FIG. 5 illustrates an image generated using the RWT helically weighting algorithm described herein with a detector width of 1.25 and a helical pitch of 7, i.e. an eight row detector. The full width half maximum (FWHM) is 1.31 mm.

While the invention has been described in terms of various specific embodiments, those skilled in the art will recognize that the invention can be practiced with modification within the spirit and scope of the claims.

What is claimed is:

1. A method for reconstructing an image of an object utilizing a computed tomographic (CT) imaging system having a radiation source and a multislice detector array on a rotating gantry, the radiation source configured to project a beam of radiation through an object and towards the multislice detector array, the multislice detector array configured to sense attenuation of the radiation passing through the object, said method comprising:

helically scanning an object with a computed tomographic imaging system with a helical pitch p that satisfies 0<p≤1.5N to acquire a plurality of slices of projection data, where N is an even integer quantity of detector rows and p is an odd integer;

generating a separate projection dataset for each of the N separate detector rows wherein the separate projection datasets comprise detector row projection data and detector row conjugate projection data;

combining the detector row projection data and the detector row conjugate projection data; and helically weighting the combined projection data using a combined helical weighting and conjugate data weighting algorithm such that a greater weight is applied to combined center row projection data than to at least one outermost detector row projection data.

2. A method in accordance with claim 1 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_r(\beta, \gamma) = \begin{cases} 0, & \beta > \beta_{r3} \\ 1 - \dfrac{\beta - \beta_{r2}}{\Delta\beta}, & \beta_{r3} > \beta > \beta_{r2} \\ 1 + \dfrac{\beta - \beta_{r2}}{\Delta\beta}, & \beta_{r2} > \beta > \beta_{r1} \\ 0, & \beta < \beta_{r1} \end{cases}$$

where:
β is a gantry angle;
γ is a fan angle;
r is a detector row;
p is a helical pitch;

$$\Delta\beta = \frac{\pi}{p};$$

$\beta_{r3} = \gamma + r\Delta\beta$;

$\beta_{r1} = \beta_{r3} + 2\Delta\beta$; and $\beta_{r2} = \beta_{r3} + \Delta\beta$.

3. A method in accordance with claim 1 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_r(\beta, \gamma) = \begin{cases} 0, & \beta > \beta_{r3} \\ 1 - \dfrac{\beta - \beta_{r2}}{\Delta\beta}, & \beta_{r3} > \beta > \beta_{r2} \\ 1 + \dfrac{\beta - \beta_{r2}}{\Delta\beta}, & \beta_{r2} > \beta > \beta_{r1} \\ 0, & \beta < \beta_{r1} \end{cases}$$

where:
 β is a gantry angle;
 γ is a fan angle;
 r is a detector row;
 p is a helical pitch;

$$\Delta\beta = \frac{\pi}{p};$$

$\beta_{r3}=\gamma+r\Delta\beta;$ $\beta_{r1}=\beta_{r3}+2\Delta\beta;$ and $\beta_{r2}=\beta_{r3}+\Delta\beta;$ when a point t(β, γ) in Radon space has a conjugate pair t'(β', γ'), where β'=β+π+2γ, and γ'=−γ.

4. A method in accordance with claim 1 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_r(\beta, \gamma) = \begin{cases} 0, & \beta > \beta_{r3} \\ 1 - \frac{\beta - \beta_{r2}}{\Delta\beta}, & \beta_{r3} > \beta > \beta_{r2} \\ 1 + \frac{\beta - \beta_{r2}}{\Delta\beta}, & \beta_{r2} > \beta > \beta_{r1} \\ 0, & \beta < \beta_{r1} \end{cases}$$

where:
 β is a gantry angle;
 γ is a fan angle;
 r is a detector row;
 p is a helical pitch;

$$\Delta\beta = \frac{2\pi}{p};$$

$\beta_{r3}=\gamma+r\Delta\beta;$ $\beta_{r1}=\beta_{r3}+2\Delta\beta;$ and $\beta_{r2}=\beta_{r3}+\Delta\beta.$

5. A method in accordance with claim 1 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_T(\beta, \gamma) = \begin{cases} 0, & \beta > \beta_{r3} \\ 1 - \frac{\beta - \beta_{r2}}{\Delta\beta}, & \beta_{r3} > \beta > \beta_{r2} \\ 1 + \frac{\beta - \beta_{r2}}{\Delta\beta}, & \beta_{r2} > \beta > \beta_{r1} \\ 0, & \beta < \beta_{r1} \end{cases}$$

where:
 β is a gantry angle;
 γ is a fan angle;
 r is a detector row;
 p is a helical pitch;

$$\Delta\beta = \frac{2\pi}{p};$$

$\beta_{r3}=\gamma+r\Delta\beta;$ $\beta_{r1}=\beta_{r3}+2\Delta\beta;$ and $\beta_{r2}=\beta_{r3}+\Delta\beta;$ when a point t(β, γ) in Radon space does not have a conjugate pair.

6. A computed tomographic (CT) imaging system for reconstructing an image of an object, said computed tomographic (CT) imaging system comprises a radiation source and a multislice detector array on a rotating gantry, said radiation source configured to project a beam of radiation through an object and towards said multislice detector array, said multislice detector array configured to sense attenuation of said radiation passing through the object;

said imaging system configured to:

helically scan an object with a computed tomographic imaging system with a helical pitch p that satisfies 0<p≦1.5N to acquire a plurality of slices of projection data, where N is an even integer quantity of detector rows and p is an odd integer;

generate a separate projection dataset for each of the N separate detector rows wherein the separate projection datasets comprise detector row projection data and detector row conjugate projection data;

combine the detector row projection data and the detector row conjugate projection data; and helically weight the combined projection data using a combined helical weighting and conjugate data weighting algorithm such that a greater weight is applied to combined center row projection data than to at least one outermost detector row projection data.

7. An imaging system in accordance with claim 6 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_T(\beta, \gamma) = \begin{cases} 0, & \beta > \beta_{r3} \\ 1 - \frac{\beta - \beta_{r2}}{\Delta\beta}, & \beta_{r3} > \beta > \beta_{r2} \\ 1 + \frac{\beta - \beta_{r2}}{\Delta\beta}, & \beta_{r2} > \beta > \beta_{r1} \\ 0, & \beta < \beta_{r1} \end{cases}$$

where:
 β is a gantry angle;
 γ is a fan angle;
 r is a detector row;
 p is a helical pitch;

$$\Delta\beta = \frac{\pi}{p};$$

$\beta_{r3}=\gamma+r\Delta\beta;$ $\beta_{r1}=\beta_{r3}+2\Delta\beta;$ and $\beta_{r2}=\beta_{r3}+\Delta\beta.$ 8. An imaging system in accordance with claim 6 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_T(\beta, \gamma) = \begin{cases} 0, & \beta > \beta_{r3} \\ 1 - \frac{\beta - \beta_{r2}}{\Delta\beta}, & \beta_{r3} > \beta > \beta_{r2} \\ 1 + \frac{\beta - \beta_{r2}}{\Delta\beta}, & \beta_{r2} > \beta > \beta_{r1} \\ 0, & \beta < \beta_{r1} \end{cases}$$

where:
β is a gantry angle;
γ is a fan angle;
r is a detector row;
p is a helical pitch;

$$\Delta\beta = \frac{\pi}{p};$$

$\beta_{r3}=\gamma+r\Delta\beta;$ $\beta_{r1}=\beta_{r3}+2\Delta\beta;$ and $\beta_{r2}=\beta_{r3}+\Delta\beta;$ when a point t(β, γ) in Radon space has a conjugate pair t'(β', γ'), where β'=β+π+2γ, and γ'=−γ.

9. An imaging system in accordance with claim 6 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_T(\beta, \gamma) = \begin{cases} 0, & \beta > \beta_{r3} \\ 1 - \frac{\beta - \beta_{r2}}{\Delta\beta}, & \beta_{r3} > \beta > \beta_{r2} \\ 1 + \frac{\beta - \beta_{r2}}{\Delta\beta}, & \beta_{r2} > \beta > \beta_{r1} \\ 0, & \beta < \beta_{r1} \end{cases}$$

where:
β is a gantry angle;
γ is a fan angle;
r is a detector row;
p is a helical pitch;

$$\Delta\beta = \frac{2\pi}{p};$$

$\beta_{r3}=\gamma+r\Delta\beta;$ $\beta_{r1}=\beta_{r3}+2\Delta\beta;$ and $\beta_{r2}=\beta_{r3}+\Delta\beta.$ 10. An imaging system in accordance with claim 6 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_T(\beta, \gamma) = \begin{cases} 0, & \beta > \beta_{r3} \\ 1 - \frac{\beta - \beta_{r2}}{\Delta\beta}, & \beta_{r3} > \beta > \beta_{r2} \\ 1 + \frac{\beta - \beta_{r2}}{\Delta\beta}, & \beta_{r2} > \beta > \beta_{r1} \\ 0, & \beta < \beta_{r1} \end{cases}$$

where:
β is a gantry angle;
γ is a fan angle;
r is a detector row;
p is a helical pitch;

$$\Delta\beta = \frac{2\pi}{p};$$

$\beta_{r3}=\gamma+r\Delta\beta;$ $\beta_{r1}=\beta_{r3}+2\Delta\beta;$ and $\beta_{r2}=\beta_{r3}+\Delta\beta;$ when a point t(β, γ) in Radon space does not have a conjugate pair.

11. A computer for collecting computed tomography (CT) scan data, said computer programmed to:
helically scan an object with a computed tomographic imaging system with a helical pitch p that satisfies 0<p≦1.5N to acquire a plurality of slices of projection data, where N is an even integer quantity of detector rows and p is an odd integer;
generate a separate projection dataset for each of the N separate detector rows wherein the separate projection datasets comprise detector row projection data and detector row conjugate projection data;
combine the detector row projection data and the detector row conjugate projection data; and
helically weight the combined projection data using a combined helical weighting and conjugate data weighting algorithm such that a greater weight is applied to combined center row projection data than to at least one outermost detector row projection data.

12. A computer in accordance with claim 11 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_r(\beta, \gamma) = \begin{cases} 0, & \beta > \beta_{r3} \\ 1 - \dfrac{\beta - \beta_{r2}}{\Delta\beta}, & \beta_{r3} > \beta > \beta_{r3} \\ 1 + \dfrac{\beta - \beta_{r2}}{\Delta\beta}, & \beta_{r2} > \beta > \beta_{r1} \\ 0, & \beta < \beta_{r1} \end{cases}$$

where:
β is a gantry angle;
γ is a fan angle;
r is a detector row;
p is a helical pitch;

$$\Delta\beta = \frac{\pi}{p};$$

$\beta_{r3} = \gamma + r\Delta\beta$;

$\beta_{r1} = \beta_{r3} + 2\Delta\beta$; and $\beta_{r2} = \beta_{r3} + \Delta\beta$.

13. A computer in accordance with claim 11 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_r(\beta, \gamma) = \begin{cases} 0, & \beta > \beta_{r3} \\ 1 - \dfrac{\beta - \beta_{r2}}{\Delta\beta}, & \beta_{r3} > \beta > \beta_{r3} \\ 1 + \dfrac{\beta - \beta_{r2}}{\Delta\beta}, & \beta_{r2} > \beta > \beta_{r1} \\ 0, & \beta < \beta_{r1} \end{cases}$$

where:
β is a gantry angle;
γ is a fan angle;
r is a detector row;
p is a helical pitch;

$$\Delta\beta = \frac{\pi}{p};$$

$\beta_{r3} = \gamma + r\Delta\beta$;

$\beta_{r1} = \beta_{r3} + 2\Delta\beta$; and $\beta_{r2} = \beta_{r3} + \Delta\beta$;

when a point t(β, γ) in Radon space has a conjugate pair t'(β', γ'), where β'=β+π+2γ, and γ'=−γ.

14. A computer in accordance with claim 11 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_r(\beta, \gamma) = \begin{cases} 0, & \beta > \beta_{r3} \\ 1 - \dfrac{\beta - \beta_{r2}}{\Delta\beta}, & \beta_{r3} > \beta > \beta_{r3} \\ 1 + \dfrac{\beta - \beta_{r2}}{\Delta\beta}, & \beta_{r2} > \beta > \beta_{r1} \\ 0, & \beta < \beta_{r1} \end{cases}$$

where:
β is a gantry angle;
γ is a fan angle;
r is a detector row;
p is a helical pitch;

$$\Delta\beta = \frac{2\pi}{p};$$

$\beta_{r3} = \gamma + r\Delta\beta$;

$\beta_{r1} = \beta_{r3} + 2\Delta\beta$; and $\beta_{r2} = \beta_{r3} + \Delta\beta$.

15. A computer in accordance with claim 11 wherein said helically weighting the combined center row projection dataset using a combined helical weighting and conjugate data weighting algorithm further comprises helically weighting the combined center row projection dataset using a combined helical weighting and conjugate data weighting algorithm in accordance with:

$$w_r(\beta, \gamma) = \begin{cases} 0, & \beta > \beta_{r3} \\ 1 - \dfrac{\beta - \beta_{r2}}{\Delta\beta}, & \beta_{r3} > \beta > \beta_{r3} \\ 1 + \dfrac{\beta - \beta_{r2}}{\Delta\beta}, & \beta_{r2} > \beta > \beta_{r1} \\ 0, & \beta < \beta_{r1} \end{cases}$$

where:
β is a gantry angle;
γ is a fan angle;
r is a detector row;
p is a helical pitch;

$$\Delta\beta = \frac{2\pi}{p};$$

$\beta_{r3} = \gamma + r\Delta\beta$;

$\beta_{r1} = \beta_{r3} + 2\Delta\beta$; and $\beta_{r2} = \beta_{r3} + \Delta\beta$;

when a point t(β, γ) in Radon space does not have a conjugate pair.

* * * * *

UNITED STATES PATENT AND TRADEMARK OFFICE
CERTIFICATE OF CORRECTION

PATENT NO.        : 7,013,034 B2
APPLICATION NO.   : 10/268323
DATED             : March 14, 2006
INVENTOR(S)       : Wang et al.

It is certified that error appears in the above-identified patent and that said Letters Patent is hereby corrected as shown below:

In Claim 12, column 11, line 5, delete

"
$$w_r(\beta,\gamma) = \begin{cases} 0, & \beta > \beta_{r3} \\ 1 - \dfrac{\beta - \beta_{r2}}{\Delta\beta}, & \beta_{r3} > \beta > \beta_{r3} \\ 1 + \dfrac{\beta - \beta_{r2}}{\Delta\beta}, & \beta_{r2} > \beta > \beta_{r1} \\ 0, & \beta < \beta_{r1} \end{cases}$$
"

and insert therefor $$w_r(\beta,\gamma) = \begin{cases} 0, & \beta > \beta_{r3} \\ 1 - \dfrac{\beta - \beta_{r2}}{\Delta\beta}, & \beta_{r3} > \beta > \beta_{r2} \\ 1 + \dfrac{\beta - \beta_{r2}}{\Delta\beta}, & \beta_{r2} > \beta > \beta_{r1} \\ 0, & \beta < \beta_{r1} \end{cases}$$
--.

UNITED STATES PATENT AND TRADEMARK OFFICE
CERTIFICATE OF CORRECTION

PATENT NO. : 7,013,034 B2
APPLICATION NO. : 10/268323
DATED : March 14, 2006
INVENTOR(S) : Wang et al.

It is certified that error appears in the above-identified patent and that said Letters Patent is hereby corrected as shown below:

In Claim 13, column 11, line 35, delete $$\text{``} \quad w_r(\beta,\gamma) = \begin{cases} 0, & \beta > \beta_{r3} \\ 1 - \dfrac{\beta - \beta_{r2}}{\Delta\beta}, & \beta_{r3} > \beta > \beta_{r3} \\ 1 + \dfrac{\beta - \beta_{r2}}{\Delta\beta}, & \beta_{r2} > \beta > \beta_{r1} \\ 0, & \beta < \beta_{r1} \end{cases} \quad \text{''}$$

and insert therefor $$\text{--} \quad w_r(\beta,\gamma) = \begin{cases} 0, & \beta > \beta_{r3} \\ 1 - \dfrac{\beta - \beta_{r2}}{\Delta\beta}, & \beta_{r3} > \beta > \beta_{r2} \\ 1 + \dfrac{\beta - \beta_{r2}}{\Delta\beta}, & \beta_{r2} > \beta > \beta_{r1} \\ 0, & \beta < \beta_{r1} \end{cases} \quad \text{--}.$$

In Claim 14, column 12, line 10, delete $$\text{``} \quad w_r(\beta,\gamma) = \begin{cases} 0, & \beta > \beta_{r3} \\ 1 - \dfrac{\beta - \beta_{r2}}{\Delta\beta}, & \beta_{r3} > \beta > \beta_{r3} \\ 1 + \dfrac{\beta - \beta_{r2}}{\Delta\beta}, & \beta_{r2} > \beta > \beta_{r1} \\ 0, & \beta < \beta_{r1} \end{cases} \quad \text{''}$$

UNITED STATES PATENT AND TRADEMARK OFFICE
CERTIFICATE OF CORRECTION

PATENT NO. : 7,013,034 B2
APPLICATION NO. : 10/268323
DATED : March 14, 2006
INVENTOR(S) : Wang et al.

It is certified that error appears in the above-identified patent and that said Letters Patent is hereby corrected as shown below:

and insert therefor $$-- w_r(\beta,\gamma) = \begin{cases} 0, & \beta > \beta_{r3} \\ 1 - \dfrac{\beta - \beta_{r2}}{\Delta\beta}, & \beta_{r3} > \beta > \beta_{r2} \\ 1 + \dfrac{\beta - \beta_{r2}}{\Delta\beta}, & \beta_{r2} > \beta > \beta_{r1} \\ 0, & \beta < \beta_{r1} \end{cases} --.$$

In Claim 15, column 12, line 40, delete $$\text{``} \quad w_r(\beta,\gamma) = \begin{cases} 0, & \beta > \beta_{r3} \\ 1 - \dfrac{\beta - \beta_{r2}}{\Delta\beta}, & \beta_{r3} > \beta > \beta_{r3} \\ 1 + \dfrac{\beta - \beta_{r2}}{\Delta\beta}, & \beta_{r2} > \beta > \beta_{r1} \\ 0, & \beta < \beta_{r1} \end{cases} \quad \text{''}$$

UNITED STATES PATENT AND TRADEMARK OFFICE
CERTIFICATE OF CORRECTION

PATENT NO. : 7,013,034 B2
APPLICATION NO. : 10/268323
DATED : March 14, 2006
INVENTOR(S) : Wang et al.

It is certified that error appears in the above-identified patent and that said Letters Patent is hereby corrected as shown below:

and insert therefor $$-- w_r(\beta,\gamma) = \begin{cases} 0, & \beta > \beta_{r3} \\ 1 - \dfrac{\beta - \beta_{r2}}{\Delta\beta}, & \beta_{r3} > \beta > \beta_{r2} \\ 1 + \dfrac{\beta - \beta_{r2}}{\Delta\beta}, & \beta_{r2} > \beta > \beta_{r1} \\ 0, & \beta < \beta_{r1} \end{cases} --.$$

Signed and Sealed this

Tenth Day of June, 2008

JON W. DUDAS
*Director of the United States Patent and Trademark Office*